(12) United States Patent
Hulliger et al.

(10) Patent No.: US 10,799,275 B2
(45) Date of Patent: Oct. 13, 2020

(54) READJUSTABLE LOCKING PLATE HOLE

(71) Applicant: DePuy Synthes Products, Inc., Raynham, MA (US)

(72) Inventors: Urs Hulliger, Oberdorf (CH); Tom Overes, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 279 days.

(21) Appl. No.: 15/824,823

(22) Filed: Nov. 28, 2017

(65) Prior Publication Data
US 2018/0078296 A1 Mar. 22, 2018

Related U.S. Application Data

(63) Continuation of application No. 12/774,308, filed on May 5, 2010, now Pat. No. 9,855,082.

(60) Provisional application No. 61/177,423, filed on May 12, 2009.

(51) Int. Cl.
*A61B 17/80* (2006.01)

(52) U.S. Cl.
CPC ...... *A61B 17/8047* (2013.01); *A61B 17/8057* (2013.01); *A61B 17/8085* (2013.01)

(58) Field of Classification Search
CPC ............ A61B 17/8047; A61B 17/8057; A61B 17/8085
See application file for complete search history.

(56) References Cited

U.S. PATENT DOCUMENTS

| | | | |
|---|---|---|---|
| 2,580,821 A | 1/1952 | Nicola | |
| 3,779,240 A | 12/1973 | Kondo | |
| 4,029,091 A | 6/1977 | von Bezold et al. | |
| 4,388,921 A * | 6/1983 | Sutter | A61B 17/8047 411/537 |
| 5,578,034 A * | 11/1996 | Estes | A61B 17/8047 411/909 |
| 5,916,200 A * | 6/1999 | Eppley | A61M 25/02 604/174 |
| 5,954,722 A * | 9/1999 | Bono | A61B 17/7059 606/281 |
| 6,506,191 B1 | 1/2003 | Joos | |
| 6,663,632 B1 * | 12/2003 | Frigg | A61B 17/80 606/246 |

(Continued)

FOREIGN PATENT DOCUMENTS

DE 3743638 7/1989
EP 0016338 10/1980

(Continued)

*Primary Examiner* — Zade Coley

(74) *Attorney, Agent, or Firm* — Fay Kaplun & Marcin, LLP

(57) ABSTRACT

A bone plate comprises a locking hole extending through the bone plate from a top surface to a bottom surface thereof. The locking hole is threaded and sized and shaped to lockingly receive a correspondingly threaded head of a bone fixation element therethrough. The bone plate further comprises a first plate relief extending at least partially through a thickness of the plate and separated from the locking hole to define a first weakened portion of the bone plate. The first plate relief extends around a portion of a circumference of the locking hole.

11 Claims, 9 Drawing Sheets

(56) References Cited

U.S. PATENT DOCUMENTS

| | | | |
|---|---|---|---|
| 6,695,846 B2* | 2/2004 | Richelsoph | A61B 17/7059 606/290 |
| 6,902,567 B2* | 6/2005 | Del Medico | A61B 17/746 411/271 |
| 6,945,975 B2* | 9/2005 | Dalton | A61B 17/7059 606/282 |
| 7,276,070 B2* | 10/2007 | Muckter | A61B 17/8047 606/71 |
| 7,311,712 B2* | 12/2007 | Dalton | A61B 17/7059 606/287 |
| 7,749,257 B2* | 7/2010 | Medoff | A61B 17/8085 606/290 |
| 7,887,569 B2* | 2/2011 | Frigg | A61B 17/80 606/280 |
| 7,981,142 B2 | 7/2011 | Konieczynski | |
| 8,262,711 B2 | 9/2012 | Hess | |
| 2001/0014807 A1 | 8/2001 | Wagner et al. | |
| 2002/0045901 A1 | 4/2002 | Wagner | |
| 2002/0151899 A1* | 10/2002 | Bailey | A61B 17/7059 606/86 B |
| 2003/0187440 A1* | 10/2003 | Richelsoph | A61B 17/7059 606/287 |
| 2003/0225409 A1* | 12/2003 | Freid | A61B 17/7059 606/281 |
| 2004/0019353 A1* | 1/2004 | Freid | A61B 17/1728 606/915 |
| 2004/0127904 A1* | 7/2004 | Konieczynski | A61B 17/8038 606/70 |
| 2004/0220570 A1* | 11/2004 | Frigg | A61B 17/80 623/17.15 |
| 2004/0267261 A1* | 12/2004 | Derouet | A61B 17/8047 606/70 |
| 2005/0004574 A1* | 1/2005 | Muckter | A61B 17/8047 606/280 |
| 2005/0015093 A1 | 1/2005 | Suh | |
| 2005/0015131 A1* | 1/2005 | Fourcault | A61B 17/7059 607/116 |
| 2005/0065521 A1 | 3/2005 | Steger | |
| 2005/0090825 A1 | 4/2005 | Pfefferle | |
| 2005/0096657 A1 | 5/2005 | Autericque et al. | |
| 2005/0234456 A1* | 10/2005 | Malandain | A61B 17/7007 606/281 |
| 2005/0273105 A1* | 12/2005 | Konieczynski | A61B 17/7059 606/289 |
| 2006/0241612 A1* | 10/2006 | Medoff | A61B 17/8085 606/287 |
| 2007/0123879 A1* | 5/2007 | Songer | A61B 17/8033 606/288 |
| 2007/0162016 A1* | 7/2007 | Matityahu | A61B 17/7059 606/281 |
| 2007/0185489 A1* | 8/2007 | Abdou | A61B 17/7059 606/255 |
| 2008/0015592 A1 | 1/2008 | Long et al. | |
| 2009/0234393 A1 | 9/2009 | Sournac | |
| 2011/0152945 A1* | 6/2011 | Matityahu | A61B 17/7059 606/290 |
| 2013/0150900 A1* | 6/2013 | Haddad | A61B 17/809 606/290 |

FOREIGN PATENT DOCUMENTS

| | | |
|---|---|---|
| EP | 0201023 | 11/1986 |
| EP | 0374084 | 6/1990 |
| FR | 2862862 | 6/2005 |
| JP | 2005/040586 | 2/2005 |
| JP | 2007/083046 | 4/2007 |
| JP | 2009/515612 | 4/2009 |
| WO | 00/36984 | 6/2000 |
| WO | 00/53111 | 9/2000 |
| WO | 02/089684 | 11/2002 |
| WO | 03/063714 | 8/2003 |
| WO | 2007/056874 | 5/2007 |
| WO | 2009/148697 | 12/2009 |

* cited by examiner

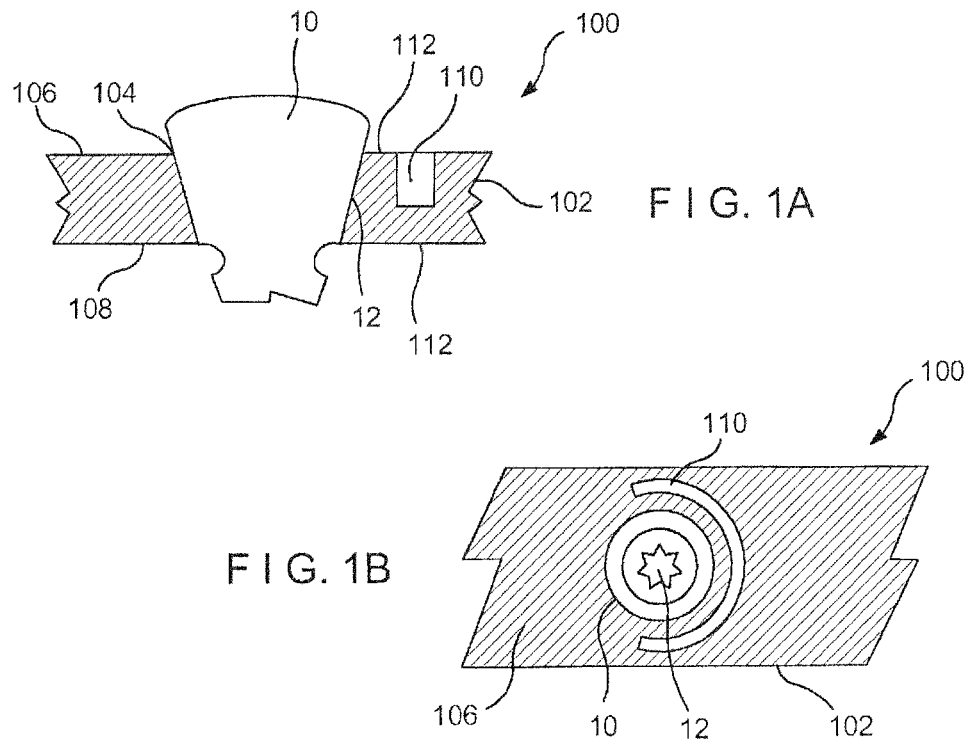
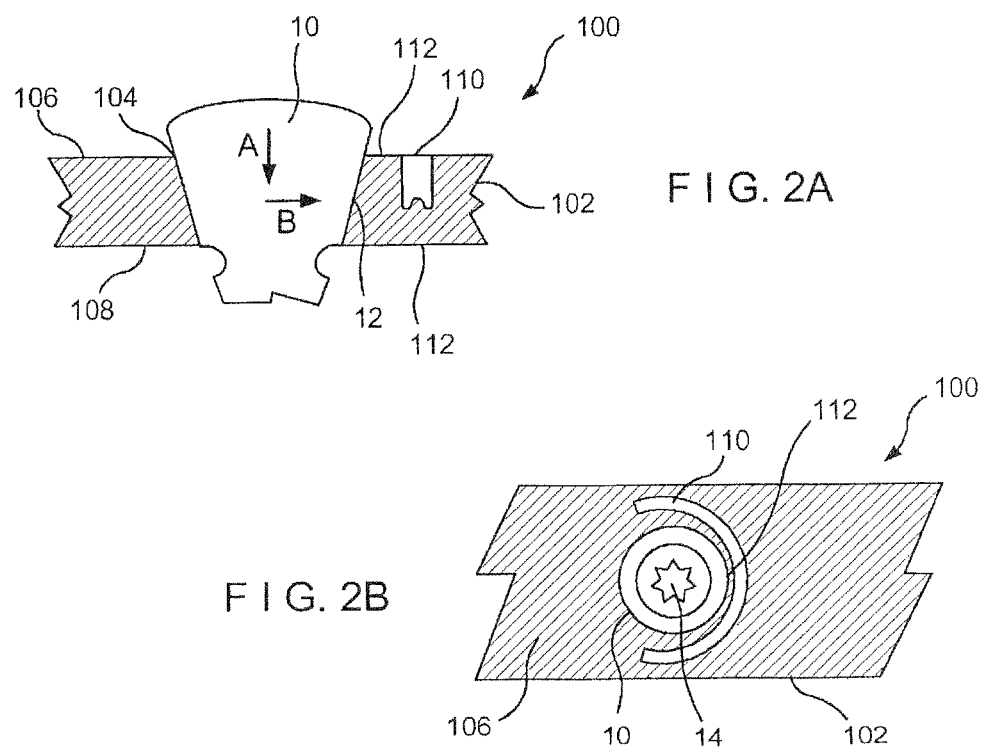

READJUSTABLE LOCKING PLATE HOLE

PRIORITY CLAIM

The present application is a Continuation of U.S. patent application Ser. No. 12/774,308 filed on May 5, 2010, now U.S. Pat. No. 9,855,082, which claims priority to U.S. Provisional Application Ser. No. 61/177,423 filed on May 12, 2009. The entire disclosures of the above patent(s)/application(s) are expressly incorporated herein by reference.

BACKGROUND INFORMATION

The repositioning and proper alignment of bone fragments is essential to effective bone fracture treatment and restoring proper bone length, axis and rotation. If fragments of the bone are misaligned force distribution across the bone is compromised, increasing of the likelihood of further injury due to excessive wear of joint surfaces, etc. resulting from the sub-optimal load distribution. Improper alignment of the bone may also have a significant impact on motion patterns of the bone and leave the bone more susceptible to further fracture.

SUMMARY OF THE INVENTION

The present invention is directed to a bone plate comprising a locking hole extending through the bone plate from a top surface to a bottom surface thereof, the locking hole being threaded and sized and shaped to lockingly receive a correspondingly threaded head of a bone fixation element therethrough in combination with a first plate relief extending at least partially through a thickness of the plate and separated from the locking hole to define a first weakened portion of the bone plate, the first plate relief extending around a portion of a circumference of the locking hole.

BRIEF DESCRIPTION OF THE DRAWINGS

FIG. 1A shows a first partial cross-sectional view of a bone plate hole according to a first embodiment of the invention;

FIG. 1B shows a top view of the bone plate hole of FIG. 1;

FIG. 2A shows a second partial cross-sectional view of the bone plate hole of FIG. 1A after the position of a screw inserted therein has been adjusted relative to its position in FIG. 1A;

FIG. 2B shows a top view of the bone plate of FIG. 1, in which the position of the screw inserted therein has been adjusted as shown in FIG. 2A;

DETAILED DESCRIPTION

Figure 3:
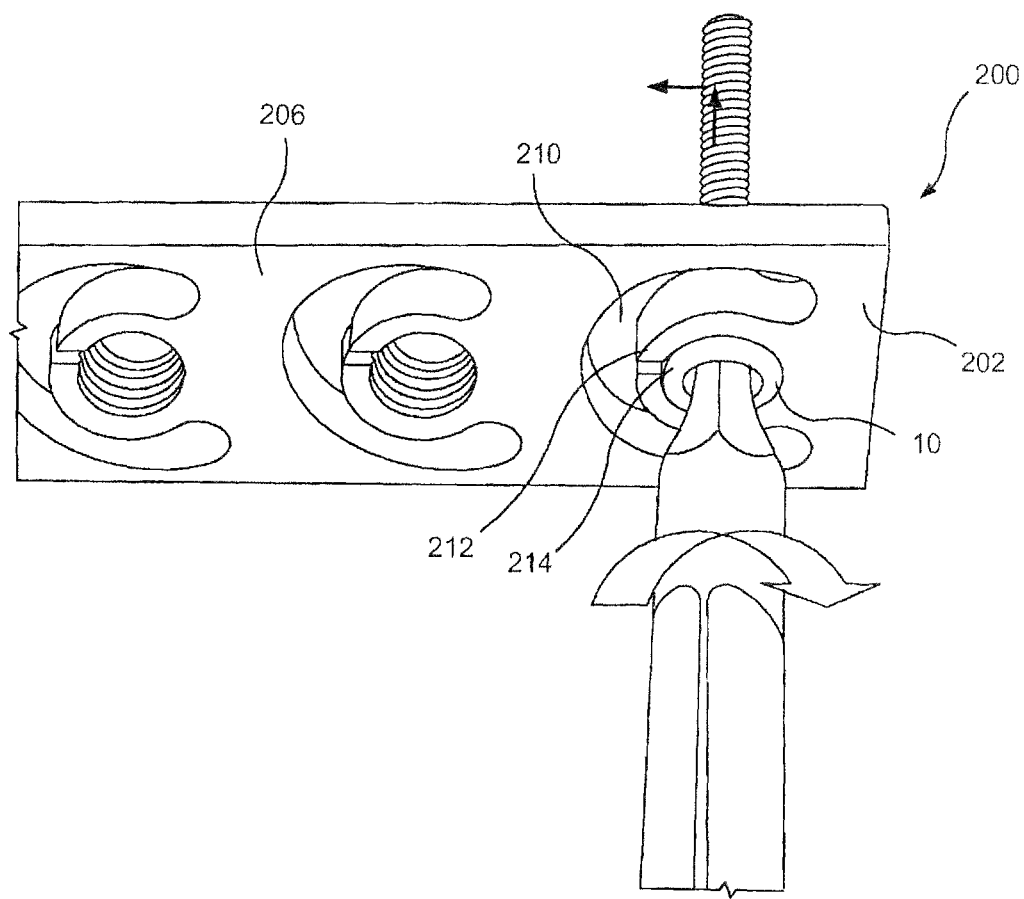
FIG. 3 shows a perspective view of a bone plate hole according to a first alternate embodiment of the invention.

The present invention may be further understood with reference to the following description and the appended drawings, wherein like elements are referred to with the same reference numerals. The present invention relates generally to systems and methods for the fixation of fractured or otherwise damaged bone. Specifically, the invention relates to a bone plate hole with a new compression relief eliminating the need for known non-locking compression holes (e.g., combination holes), as will be described in more detail below. Specifically, conventional compression holes engage screws inserted therethrough with an angled surface that forces the screw axis in a particular direction as the screw is further driven into the bone to apply compressive forces between bone fragments coupled to the plate. However, the angled surfaces and the movement of the head of the screw relative thereto do not permit the screw to be locked in position (e.g., threadedly engaged) in the bone plate. The exemplary bone plate hole according to the present invention can lock the screw to the plate while permitting minor adjustments in the position/orientation of the screw relative to the plate to reposition bone fragments coupled thereto after the bone plate has been positioned and locked thereagainst. Specifically, plate holes according to the present invention permit a physician to pivot a bone screw after insertion into the hone to adjust the position of a portion of bone coupled thereto, as will be described in greater detail hereinafter. Those skilled in the art will understand that, as used in this application, the term top refers to a portion of the device which, in an operative position, faces away from a bone to which it is being applied while bottom refers to portions of the device which, in the operative position, face the bone.

As shown in FIGS. 1A-2B, a system 100 according to an exemplary embodiment of die invention comprises a plate body 102 formed with a plate hole 104 extending therethrough from a top surface 106 to a bottom surface 108. The plate hole 104 is substantially conical with its larger diameter at the top surface. The taper angle of the plate hole 104 is preferably in the range of 10° to 30°, wherein the upper limit indicates a maximum lateral degree of movement of a bone screw 10 inserted therethrough. However, as would be understood by those skilled in the art, any taper angle in the range of 0-90° may also be employed, wherein the maximum taper angle is selected to maintain a head of the bone screw 10 in a locked position within the plate. A compression relief 110 is formed on the plate body 102 adjacent the plate hole 104. The compression relief 110 extends into the plate body 102 by a predetermined depth. In an exemplary embodiment, the compression relief 110 comprises an arced slot extending into the top surface along an arc length spanning at least half of the diameter of the plate hole 104. In another embodiment of the present invention, the compression relief 110 may extend over an arc of approximately 90°-270° relative to the plate hole 104, wherein a selected length depends on one or more of the material properties of the plate body 102 and an intended implantation site within the living body. Specifically, when the plate body 102 is positioned over a bone with a high density, the compression relief 110 may have a greater arc length than when positioned over a bone with a low density, the increased length permitting greater force absorption by the compression relief 110, as will be described in greater detail hereinafter. In the embodiment of FIGS. 1A-2B, the compression relief 110 is substantially concentric with the plate hole 104 when in an unstressed state and extends around approximately one half of its circumference to permit deflection of a bone screw 10 inserted through the plate hole 104 toward the compression relief 110. Accordingly, the compression relief 110 is preferably positioned relative to the plate hole 104 in a manner facilitating deflection of a portion of the plate body 102 between an edge of the plate hole 104 and the adjacent relief 110 in a direction toward the relief 110. As shown below, compression reliefs according to the invention may assume any of a variety of shapes and positions relative to the plate hole 104 and are not restricted to the partial circumferential shape of the compression relief 110 of FIGS. 1A-2B.

The plate body 102 may be made of any suitable material including, but not limited to, a compound plastic, polyaryletheretherketone ("PEEK"), stainless steel, a cobalt chrome alloy, titanium, a titanium alloy, etc., as those skilled in the art will understand. The material selected for the plate body 102 must be biocompatible and must exhibit the rigidity required to withstand the forces which will be exerted thereupon during and after attachment to a bone as would be understood by those skilled in the art. The compression relief 110 serves to reduce a rigidity of a portion of the plate body 102 adjacent to the plate holes 104 and, more specifically, of the portion of the plate body 102 lying between the compression relief 110 and adjacent the plate hole 104. Specifically, the compression relief 110 defines a reduced thickness portion 112 of the plate body 102 adjacent to the plate hole 104 that is more flexible than portions of the plate body 102 adjacent to the plate hole 104 which are not surrounded by the compression relief. Thus, when a laterally directed force is applied to the plate hole 104 via the bone screw 104, as will be described in greater detail later on, the reduced thickness portions 112 deform toward the reliefs 110 as shown in FIGS. 2A and 2B. A driver (not shown) configured to engage a respectively sized slot 14 on the head 12, is used to screw the bone screw 10 into the plate hole 104. As the tapered head 12 of the bone screw 10 advances into the plate hole 104 in the direction A, the head 12 exerts an increasing amount of radially outwardly directed force against the portion of the plate body 102 adjacent thereto. The increased force causes the reduced thickness portion 112 to deform moving the portion of the plate hole 104 adjacent the top surface 106 radially outward toward the relief 110, as shown in FIG. 2A. Specifically, the deflection causes the screw axis to move in the direction B to generate a compressive force between the bone fragment into which the screw 10 has been driven and an adjacent bone fragment (not shown) immediately to the right thereof (as seen in FIG. 2A). Deformation of the compression relief 110 also absorbs some of the pressure exerted by the screwing of the bone screw 10 during insertion. The inner surface of the plate holes 104 may be threaded to lock the screws 10 in place therein.

FIG. 3 depicts a system 200 according to another embodiment of the present invention. The system 200 is formed substantially similarly to the system 100 with the exception of a compression relief 210 which extends entirely through plate body 202 so that the portions of the plate body 202 surrounding plate holes 204 are coupled to the rest of the plate body only at bridge portions 212 formed around a portion of the circumference of the plate holes 204 not surrounded by the compression reliefs 210. In an exemplary embodiment, the compression relief 210 is substantially concentric with the plate hole 204 and extends around more than one half of the circumference of the plate hole 204. In an alternate embodiment, the compression relief 210 may extend across any portion of a circumference of the plate hole 204. As described in greater detail above, the location of the compression relief 210 relative to the plate hole 204 determines a deflection direction of a bone screw inserted into the plate hole 204. A relief slit 214 may be formed through the material surrounding the plate hole 204 diametrically opposed to the bridge portion 212 to permit the hole to be enlarged slightly as the screw 10 is inserted thereinto. It is noted, however, that the relief slit 214 may be oriented in any direction desired without deviating from the spirit and scope of the present invention. In a first configuration, walls of the bridge portion 212 adjacent to the relief slit 214 are in contact with one another when the plate hole 204 is in an unstressed state. When a radially expansive pressure is applied thereto during the insertion of a bone screw 10, the relief slit 214 expands deforming the bridge portion 212 and the compression relief 210.

Figure 4A:
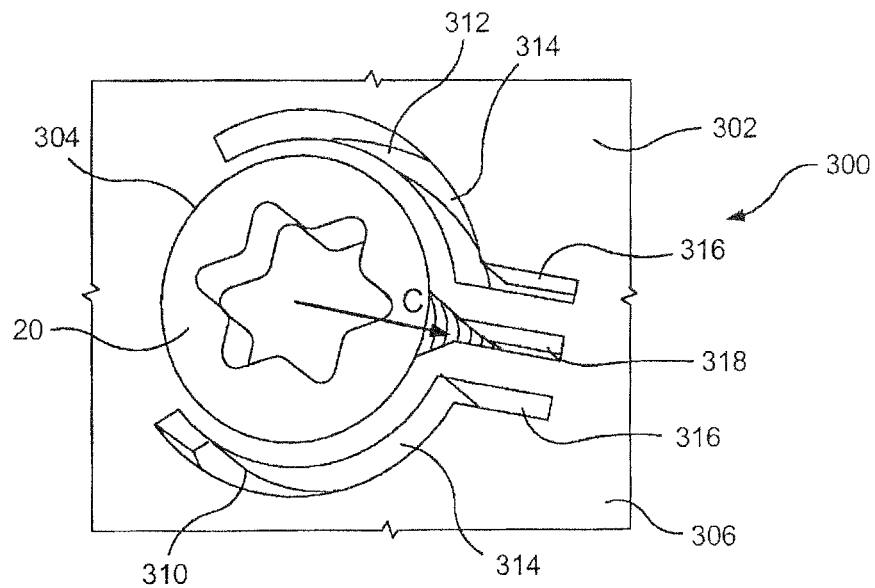
FIG. 4A shows a top view of a bone plate hole according to a second alternate embodiment of the invention.
Figure 4B:
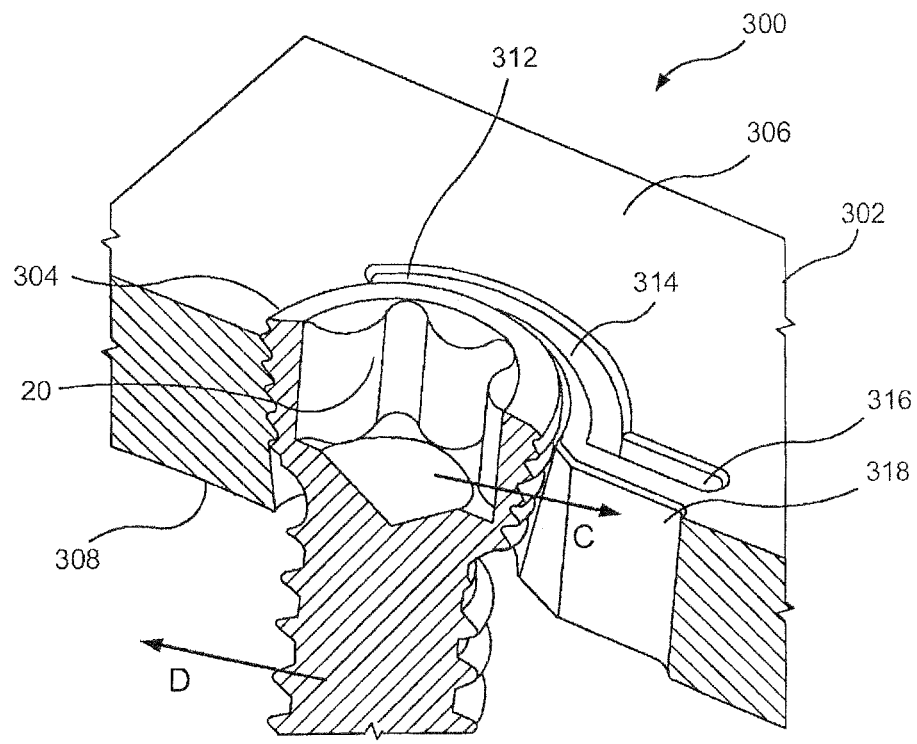
FIG. 4B shows a partial cross-sectional view of the bone plate hole of FIG. 4A.

As shown in FIGS. 4A-4B, a system 300 according to another embodiment of the invention includes a plate body 302 with a plate hole 304 substantially similar to the plate hole 204 of FIG. 3 except that the compression relief has been separated into first and second compression reliefs 310, 312 each bordering a periphery of the plate hole 304. The first and second compression reliefs 310, 312 which extend through the plate body 302 from a top surface 306 to a bottom surface 308. Similar to the compression relief 210 of FIG. 3 each of the first and second compression reliefs 310, 312 extend along an arc portion 314 to a longitudinal portion 316 extending away from the plate hole 304 by a predetermined length. The longitudinal portions 316 of each of the first and second compression reliefs 310, 312 are parallel to one another and separated from one another by an extension 318 of the plate hole 304 abutting radially outward from the plate hole 304 a predetermined distance substantially similar to a length of each of the longitudinal portions 316.

The extension 318 allows for the radial expansion of the plate hole 304 in a manner similar to the relief slit 214 while the first and second compression reliefs 310, 312 allow for movement of the head of a bone screw 20 in the direction of the arrow C. Specifically, as the bone screw 20 is being inserted into the plate hole 304 and threadedly locked therein, pressure may be applied to the periphery of the plate hole 304 to deform the material between the compression reliefs 310, 312, rotation of the screw 20 causing a top surface of the head thereof to deflect laterally in the direction of the arrow C while the shaft of the screw 20 deflects laterally in the direction D. Thus, the screw 20 assumes an angle within the bone that is not perpendicular to the plane of the plate body 302. Accordingly, the longitudinal portions 316 and the extension 318 may be selectively angled and positioned to permit movement of the bone screw 20 in a desired direction of the plate body 302, as those skilled in the art will understand.

Figure 5A:
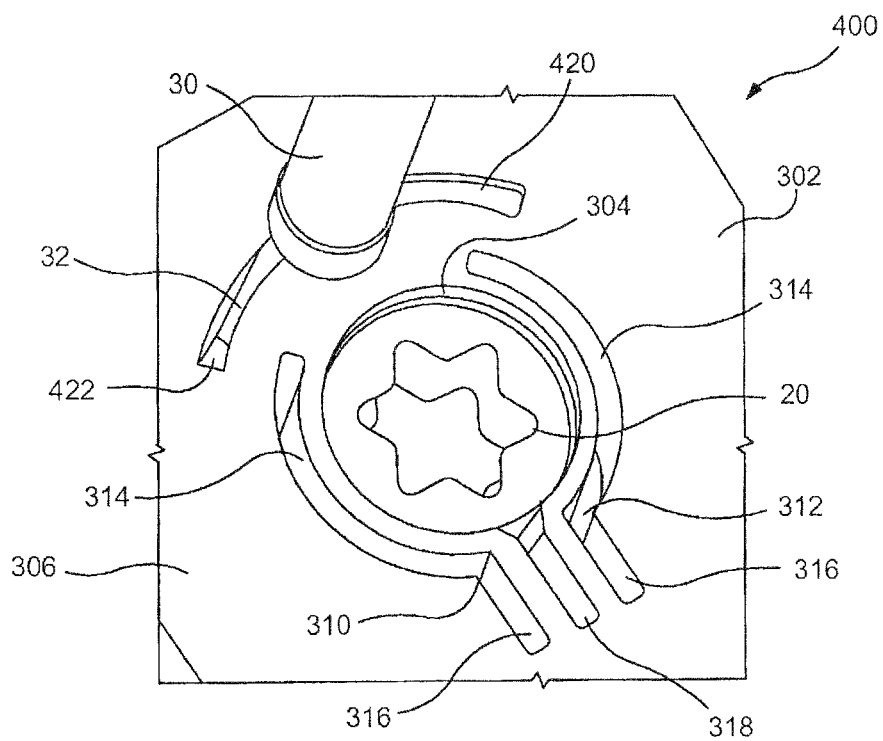
FIG. 5A shows a top view of a bone plate hole according to a third alternate embodiment of the invention.
Figure 5B:
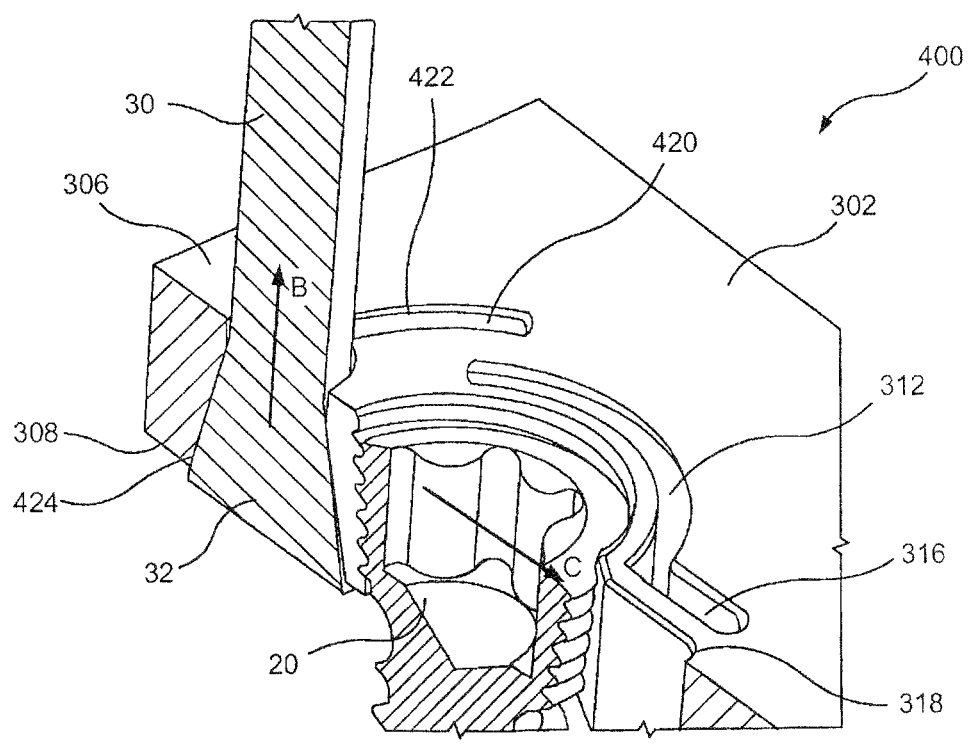
FIG. 5B shows a partial cross-sectional view of the bone plate hole of FIG. 5A.

In yet another embodiment of the present invention, as shown in FIGS. 5A and 5B, a system 400 may be formed substantially similarly to the system 300 of FIGS. 4A-4B with the exception of an additional driver hole 420 formed on a side of the plate hole 304 substantially opposite a desired direction of movement of the bone screw 20. Specifically, as discussed earlier, the compression reliefs 310, 312 allow the plate body 302 to be deformed so that the head of the bone screw 20 may be moved toward the longitudinal portions 316 and extension 318 of the compression reliefs 310, 312. The driver hole 420 includes a substantially conical, threaded first portion 424 sized to receive a correspondingly shaped conical bolt 32 with an arced slot 422 extending on either side of this first portion 424. After the screw 20 has been inserted through a plate hole 304 into the bone, its position may be adjusted by rotating the conical bolt 32 to draw it further through the first portion 424 of the driver hole 420 toward the top surface of the plate body 302. This brings increasingly larger portions of the conical bolt 32 into the driver hole 420 deforming the portion of the plate body 302 between the driver hole 420 and the plate hole 304 and forcing the head of the screw 20 to move away from the driver hole 420 in a manner similar to that described above. The driver hole 420 is preferably substantially centered with respect to a desired direction of movement of the bone screw 20.

Figure 6A:
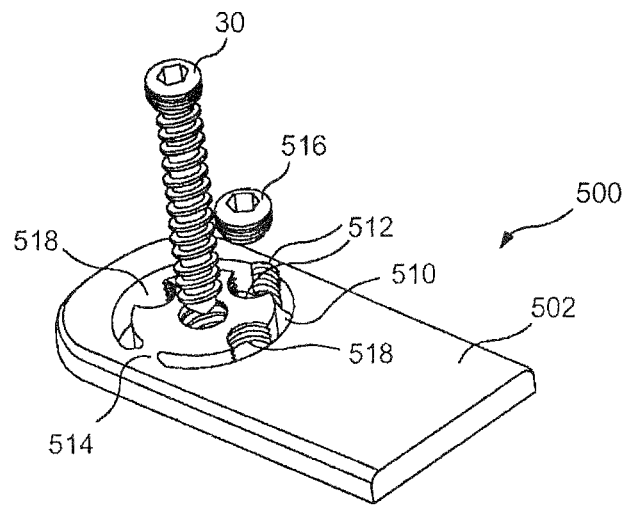
FIG. 6A shows a first perspective view of a bone plate hole according to a fourth alternate embodiment of the present invention.
Figure 6B:
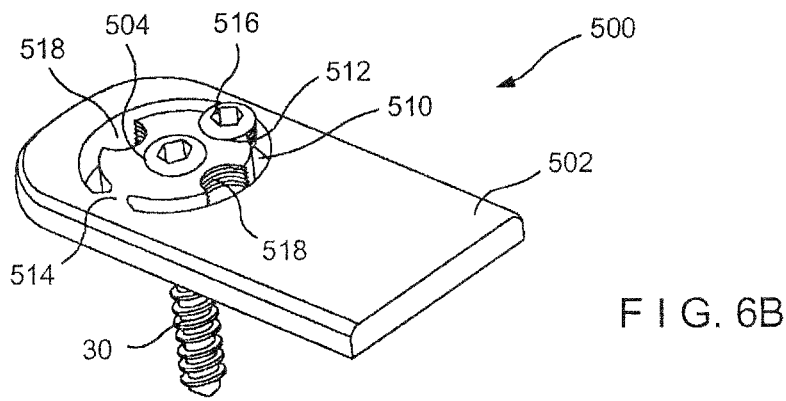
FIG. 6B shows a second perspective view of the bone plate hole of FIG. 6A.
Figure 6C:
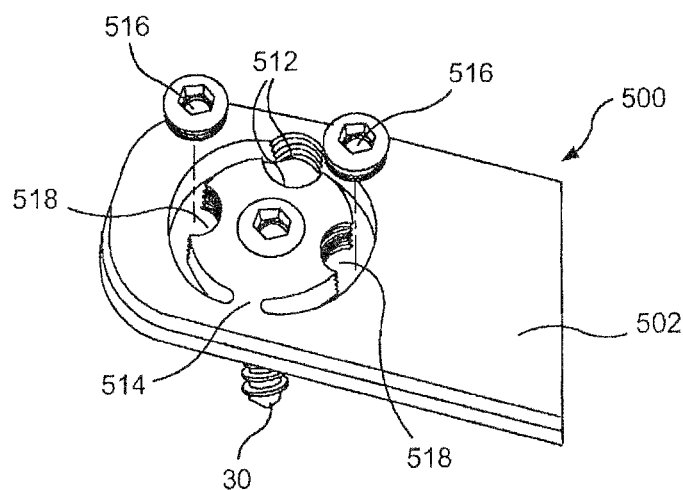
FIG. 6C shows a third perspective view of the bone plate hole of FIG. 6A.

As shown in FIGS. 6A-6C, a system 500 according to another embodiment of the invention includes a compression relief 510 of a bone plate 502 configured to allow a user to select a direction of movement of a bone screw 30 inserted therethrough. The plate hole 504 and compression relief 510 are formed substantially similarly to the plate hole 104 and compression relief 110 of FIGS. 1A-2B while the portion of the plate body 502 remaining between the plate hole 504 and the compression relief 510 includes a first recess 512 including threading on both inner and outer walls of the compression relief 510. The first recess is sized and shaped to engage a substantially conical spacer 516 therein to lock the plate hole 504 in the neutral position (i.e., the position it remains in when unstressed). Insertion of a spacer 516 into the first recesses 512 prevents the deformation of the plate hole 504 and a screw 20 therein away from a neutral position.

The plate hole 504 also includes a plurality of second recesses 518 distributed about the circumference of the plate hole 504. The second recesses 518 include conical threaded portions on the inner wall of the compression relief 510 (i.e., the portion of the plate body 502 between the plate hole 504 and the compression relief 510) but the adjacent portions of the outer wall of the compression relief 510 are not recessed. Specifically, since the size of the opening defined by each second indentation 518 is smaller than a diameter of the spacer 516, the spacer 516 applies a compressive force to the plate hole 504 during insertion. The conical shape of the spacers 516 permits the application of increasing compressive force as the spacer 516 is screwed further into the second indentations 518. In a preferred method according to the present invention, a user may screw a spacer 516 into a selected one of the first or second indentations 512, 518 to permit biasing of the bone screw 30 in an opposite direction, as described earlier. Thus, insertion of a spacer 516 into one of the second recesses 518 deforms the plate body 502 pushing the plate hole 504 and the screw 20 therein away from the spacer 516. The distribution of second recesses 518 around the circumference of the plate hole 504 allows a user to select a direction of compression to be applied. Those skilled in the art will understand that the recesses 512 may be distributed about the circumference of the plate hole 504 in any desired pattern to facilitate the application of compressive forces in the desired directions.

Figure 7:
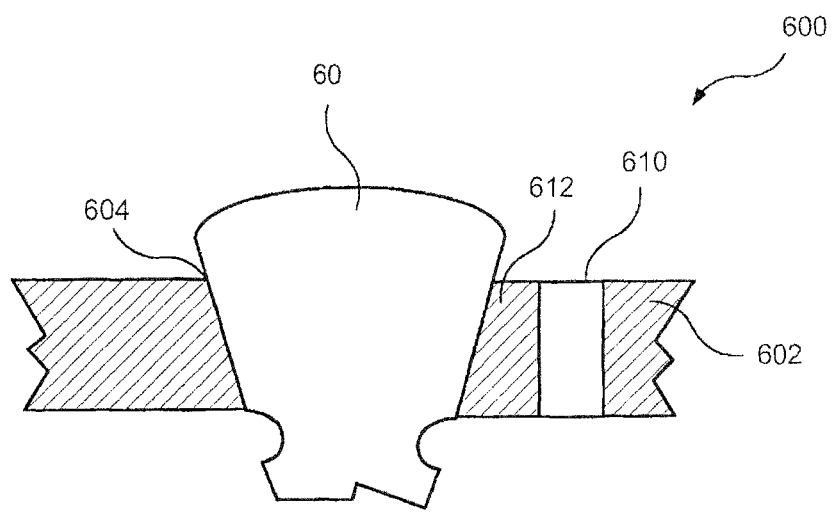
FIG. 7 shows a partial cross-sectional view of a bone plate hole according to a fifth alternate embodiment of the present invention.

FIG. 7 depicts a system 600 according to yet another embodiment of the present invention. The system 600 is formed substantially similarly to the system 100 with the exception of a compression portion 610 positioned adjacent a plate hole 604 extending through a plate body 602. Specifically, instead of a compression relief extending partially or completely through the plate body 602, the compression portion 610 is provided in a region bordering the compression hole 604 in the same manner as the compression relief 110 of FIG. 1. The compression portion 610 is formed of a material with a substantially lower density than the plate body 602, thus permitting compression thereof and allowing the deflection of a bone screw 60 in a direction approaching the compression region, as described in greater detail earlier. An exemplary material for the compression portion 610 is one of a meshed metal or another material with high porosity. The exemplary embodiment of the present invention permits lateral movement and locking of the bone screw 60 within the plate body 602 in the same manner as the system 100 while also preventing tissue ingrowth into the plate body 602, as those skilled in the art will understand. Those skilled in the art will understand that the compression portion 610 may be shaped and located in the same manner as any of the compression reliefs described above or in any other suitable fashion without deviating from the scope of the invention.

Figure 8A:
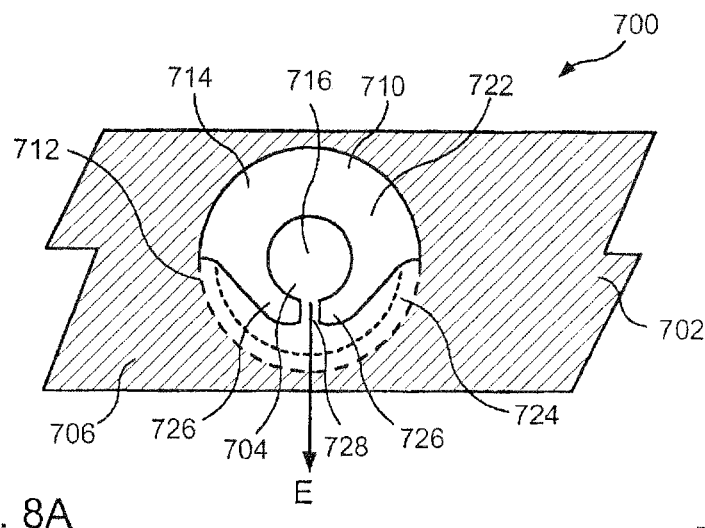
FIG. 8A shows a first top view of a bone plate hole according to a sixth alternate embodiment of the present invention.
Figure 8B:
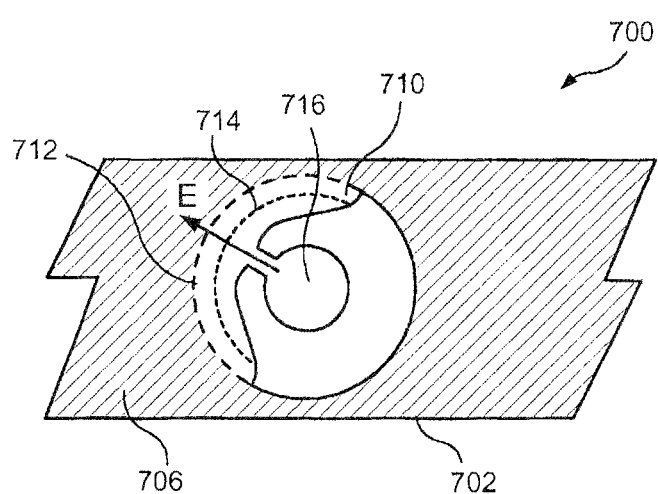
FIG. 8B shows a second top view of the bone plate hole of FIG. 8A.
Figure 8C:
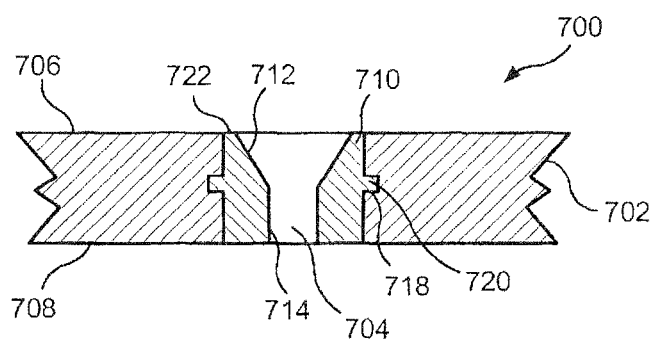
FIG. 8C shows a partial cross-sectional view of the bone plate hole of FIG. 8A.

FIGS. 8A-8C depict another embodiment of the present invention, wherein a system 700 comprises a plate body 702 having a plate hole 704 extending therethrough, the plate hole 704 receiving a compression insert 710. The plate hole 704 is substantially cylindrical and extends from a top surface 706 to a bottom surface 708 with a hole axis of the plate hole 704 being, for example, substantially perpendicular to a longitudinal axis of the plate body 702. The plate hole 704 further comprises a recess 718 extending into a wall thereof, for example, substantially equidistant from the top and bottom surfaces 706, 708, respectively, of the plate body 702. The recess 718 is sized and shaped to rotatably engage a circular flange 720 of the compression insert 710, which may be positioned therein during manufacturing. The compression insert 710 is concentrically received within the plate hole 704 so that an axis of an opening 716 extending through the compression insert 710 is aligned with the plate hole 704 axis. The opening 716 through the compression insert 710 comprises a first conical portion 712 extending a predetermined distance from the proximal surface 706 and a second cylindrical portion 714 extending from the first conical portion 712 to the distal surface 708. The second cylindrical portion 714 may be threaded to permit screwing of a bone fixation element (not shown) thereinto.

A top surface 722 of the compression insert 710 has a substantially circular cross-section with the opening 716 extending through a center thereof. A compression relief 724 extends into the top surface 722 along an arc length spanning, for example, half of the diameter of the plate hole 704 or more. It is noted, however, that the compression relief 724 may extend over any portion of the plate hole 704 without deviating from the scope of the present invention. The compression relief 724 further defines a bridge portion 726 extending around a portion of the circumference of the plate hole 704 surrounded by the compression relief 724, the bridge portion 726 comprises a reduced thickness portion of the top surface 722. Unlike the compression reliefs discussed in earlier embodiments, the compression relief 724 may be crescent-shaped with a non-uniform thickness. A relief slot 728 may be formed in the top surface 722 extending through the bridge portion 726 connecting the opening 716 to the compression relief 724. Like the relief slit 214 of the system 200, the relief slot 728 is configured to permit the opening 716 to be enlarged slightly as the bone screw (not shown) is inserted thereinto. As a radially expansive pressure is applied thereto during the insertion of a bone screw into the first conical portion 712, the relief slot 728 expands, deforming the bridge portion 726 and the compression relief 724. The expansion allows a head of the bone screw to move in the direction E. The exemplary embodiment of the present invention permits a physician or other user to rotate the compression insert 710 before or after the plate body 702 has been placed on a target implantation site to select a direction E of movement of a bone screw (not shown) inserted therethrough, as shown in FIGS. 8A and 8B to select a resultant force on the plate body 702 as will be understood by those skilled in the art. An exemplary method for the system 700 is substantially the same as discussed in earlier embodiments. Once the bone screw has been screwed into the opening 716, lateral movement of the hone screw in the direction E prevents further rotation of the compression insert 710.

Figure 9A:
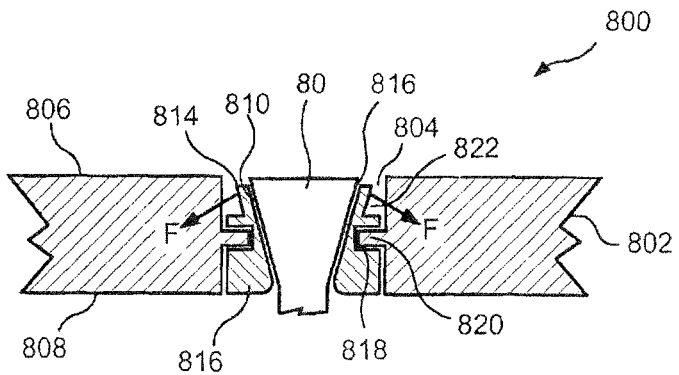
FIG. 9A shows a partial cross-sectional view of a bone plate hole according to a seventh alternate embodiment of the present invention.
Figure 9B:
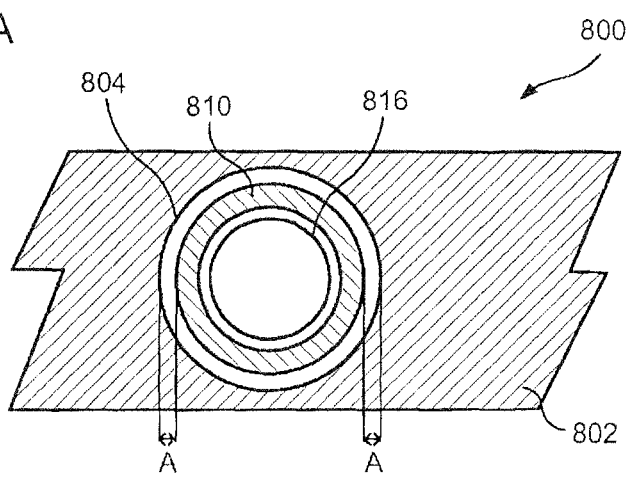
FIG. 9B shows a first top view of the bone plate hole of FIG. 9A.
Figure 9C:
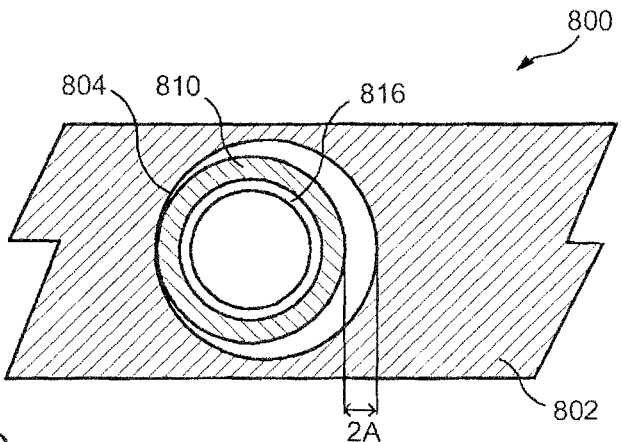
FIG. 9C shows a second top view of the bone plate hole of FIG. 9A.

As shown in FIGS. 9A-9C, a system 800 according to a further embodiment of the invention comprises an insert 810 formed substantially similarly to the insert 710 of FIGS. 8A-8C with the exception of the dimensions and mechanical properties thereof. Specifically, the insert 810 is inserted into a plate hole 804 extending through a plate body 802. A groove 818 formed on an outer wall of the insert 810 is configured to rotatably engage a flange 820 extending from a wall of the plate hole 804. The groove 818 is formed with dimensions that permit loose engagement with the flange 820 sufficient to permit the insert 810 from sliding out of engagement with the plate body 802 while also permitting rotation relative to the plate body 802 and a degree of lateral and longitudinal movement of the insert 810 relative to the plate body 802. Specifically, the insert 810 is sized and shaped such that, when inserted within the plate hole 804, a gap with a length A is formed between the plate hole and the insert 810, as shown in the top view of FIG. 9B. A length of the groove 818 is therefore at least larger than the length A to prevent the insert 810 from sliding out of the plate hole 804. One or both of the groove 818 and the flange 820 comprises a grooved or etched surface to increase friction therebetween. The insert 810 further comprises a substantially conical opening 816 extending therethrough from a proximal surface 806 of the plate body 802 to a distal surface 808, dimensions of the conical opening 816 being configured to match those of the head of a bone screw (not shown) to be inserted therethrough. An outer diameter of a proximal portion 814 of the insert 810 is selected to be smaller than a diameter of the plate hole 804 to define a substantially symmetrical annular space 822 therebetween. The reduction in diameter weakens the proximal portion 814 so that the proximal portion 814 is deflectable into the empty space 822 when subjected to a pressure by the head of a bone fixation element 80. A distal portion 816 of the insert 810 has a diameter sufficient to permit rotatable insertion thereof into the plate hole 804 with a minimal amount of lateral movement. Furthermore, the conical opening 816 may be threaded to engage threads on the head of the bone screw.

In accordance with an exemplary method for the system 800, the bone fixation element 80 is inserted into the opening 816, wherein the insert 810 is positioned within the plate hole 804. For example, the insert 810 may initially be centered within the plate hole 804. After the bone fixation element 80 has been inserted therethrough to a predetermined depth, the bone fixation element 80 and insert 810 may be biased along a side of the plate hole 810 so that, for example, a length 2A remains on the opposite side thereof. In this position, a longitudinal axis of the bone fixation element 80 is deviated from a longitudinal axis of the plate hole 804. Furthermore, pivoting of the bone screw in the aforementioned manner locks a position thereof within the bone in the same manner as described in earlier embodiments. Specifically, as the head of the bone fixation element 80 is screwed distally into the opening 816, radially outwardly directed pressure is applied by the head on the insert 810 causing the proximal portion 814 to deflect radially outward into the annular space 822 in the direction F. Specifically, the proximal portion 814 expands radially outward upon receipt of the pressure from the bone fixation element 80. The deflection causes the proximal portion 814 to apply a constrictive pressure on the flange 820 to lock the bone fixation element 80 within the plate hole 804 and also prevent rotation of the insert 810. Thus, this embodiment permits a user to pivot the bone screw (not shown) in any direction within the plate hole 804.

Figure 10:
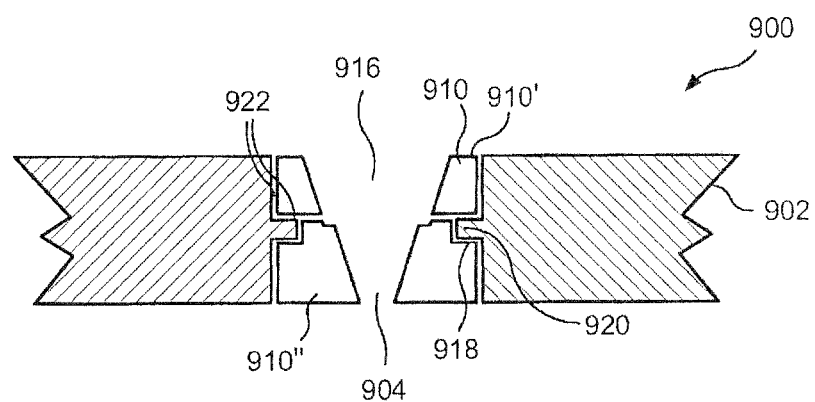
FIG. 10 shows a partial cross-sectional view of a bone plate hole according to an eighth alternate embodiment of the present invention.

As shown in FIG. 10, a system 900 according to another embodiment of the invention is formed substantially similarly to the system 800 except that an insert 910 is formed of first and second parts 910', 910" cooperating to function in the same manner described above for the system 800. Furthermore, the insert 910 does not comprise an annular space extending around a proximal portion thereof. The combined first and second parts 910', 910" form an opening 916 substantially similar to the opening 816. The second insert 910" comprises a flange groove 918 configured to engage a flange 920 of a plate body 902. An exemplary method for the system 900 is substantially similar to the method discussed above with respect to FIGS. 9A-9C, wherein a compressive force applied by the first and second inserts 910', 910" on the flange 920 locks a position of a bone screw and prevents further rotation of the first and second inserts 910', 910" relative thereto.

In an alternate embodiment of the present invention, each of the plate holes and respective compression reliefs may be formed of any shape known in the art. Furthermore, additional or lesser compression reliefs may be employed without deviating from the scope of the present invention. In another embodiment (not shown), the compression relief of the present invention may be used in a bone plate with a variable angle plate hole, as those skilled in the art will understand.

It will be apparent to those skilled in the art that various other modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A bone plate, comprising:
   a bone fixation element hole extending through the bone plate from a top surface to a bottom surface thereof;
   an insert rotatably received within the bone fixation element hole, an opening extending through the insert being sized and shaped to receive a head of a bone fixation element therethrough; and
   a first plate relief extending at least partially through a thickness of the insert to define a first weakened portion of the insert, the first plate relief extending around a portion of a circumference of the insert, the insert defining a weakened area facing the first plate relief, the weakened area defining a direction of deflection of a bone fixation element into the bone fixation element receiving hole so that a rotational orientation of the insert within the bone fixation plate defines a direction of deflection of a bone screw received within the bone fixation receiving hole relative to the bone plate.

2. The bone plate of claim 1, the first plate relief extends from the top surface of the insert to a predetermined depth therein and wherein the first plate relief extends along a portion of a circle substantially concentric with the locking bone fixation element hole.

3. The bone plate of claim 2, wherein the locking hole comprises a groove extending into a wall thereof configured to engage a flange extending from an outer periphery of the insert.

4. The bone plate of claim 2, wherein a portion of the insert bordering the first plate relief locking hole forms a bridge portion defining weakened portions of the insert deflectable under pressure from a bone fixation element.

5. The bone plate of claim 4, further comprising a slot extending from the first plate relief to the opening of the insert, a direction of the slot defining a direction of the deflection of the opening.

6. The bone plate of claim 1, wherein the opening extending through the insert is substantially conical with a diameter thereof at the top surface greater than a diameter thereof at the bottom surface.

7. The bone plate of claim 1, wherein the first plate relief is formed as a groove extending around a portion of a periphery of the insert.

8. The bone plate of claim 7, wherein the first plate relief is configured to engage a flange located on a wall of the locking hole.

9. The bone plate of claim 7, wherein the weakened portion of the insert is configured to deflect radially outward when a bone fixation element is inserted thereinto to apply a constrictive pressure on the flange.

10. The bone plate of claim 1, wherein the weakened portion of the insert is a slot configured to extend from the opening to the first plate relief.

11. The bone plate of claim 1, wherein the first plate relief is configured to allow a user to select a direction of movement of a bone fixation element inserted therethrough.

* * * * *